United States Patent [19]

Wheeler

[11] 4,291,057

[45] Sep. 22, 1981

[54] BIOCIDAL ESTERS OF HALO-4-ALKENOIC ACIDS

[75] Inventor: Thomas N. Wheeler, Charleston, W. Va.

[73] Assignee: Union Carbide Corporation, New York, N.Y.

[21] Appl. No.: 54,212

[22] Filed: Jul. 2, 1979

[51] Int. Cl.$^3$ .................... A01N 37/06; C07C 57/03
[52] U.S. Cl. .................... 424/304; 560/152;
560/156; 260/326 A; 560/172; 560/183;
260/326 N; 560/219; 560/221; 260/326 S;
260/347.2; 260/347.4; 260/400; 260/401;
260/402; 260/402.5; 260/404; 260/405;
260/405.5; 260/465 D; 424/274; 424/275;
424/285; 424/305; 424/307; 549/65; 549/66;
549/77; 549/79; 560/61; 560/62; 560/63;
560/118; 560/122; 560/124; 560/125; 560/126;
560/128; 560/150

[58] Field of Search ........... 260/326 A, 326 N, 326 S, 260/347.2, 347.4, 399, 400, 401, 402, 402.5, 404, 405, 405.5, 465 D; 424/274, 275, 285, 304, 305, 307; 549/65, 66, 77, 79; 560/61, 62, 63, 118, 122, 124, 125, 126, 128, 150, 152, 156, 172, 183, 219, 221

[56] References Cited

U.S. PATENT DOCUMENTS

| | | | |
|---|---|---|---|
| 3,996,244 | 12/1976 | Fujimoto et al. | 560/221 X |
| 4,042,710 | 8/1977 | Bull et al. | 560/221 X |
| 4,161,536 | 7/1979 | Drabek et al. | 560/219 X |

FOREIGN PATENT DOCUMENTS

| | | |
|---|---|---|
| 860687 | 5/1978 | Belgium . |
| 862499 | 6/1978 | Belgium . |
| 2810031 | 9/1978 | Fed. Rep. of Germany ...... 560/219 |

*Primary Examiner*—Richard Raymond
*Attorney, Agent, or Firm*—Robert C. Brown; William R. Moran; Clement J. Vicari

[57] ABSTRACT

Novel esters of halo-4-alkenoic acid compounds having pesticidal activity and methods of their preparation.

23 Claims, No Drawings

BIOCIDAL ESTERS OF HALO-4-ALKENOIC ACIDS

BACKGROUND OF THE INVENTION

1. Field of the Invention

This invention relates to novel esters of halo-4-alkenoic acid compounds having pesticidal activity and methods of their preparation.

2. Description of the Prior Art

Esters of isovaleric acid are disclosed in U.S. Pat. No. 4,042,710, including 2- substituted isovalerates having the structural formula I:

$$\text{I} \quad \underset{H_3C\phantom{xx}CH_3}{\diagdown\!\!\diagup} \\ R-CH-\overset{O}{\underset{\|}{C}}-O-\overset{X}{\underset{|}{CH}}-Y$$

in which R represents an alkyl group of 1 to 16 carbon atoms (which may be branched), an alkenyl group of up to 6 carbon atoms, or a benzyl group optionally substituted by one or more halogen atoms.

U.S. Pat. Nos. 4,039,680; 4,062,968; and 4,058,622 all disclose esters having the general structure II:

$$\text{II} \quad \underset{R_8\phantom{xx}R_7}{\diagdown\!\!\diagup C=C\diagdown} \\ \phantom{xxxxx}\underset{R_9}{\diagup}\phantom{xx}\overset{Z}{\underset{|}{CH}}-\overset{O}{\underset{\|}{C}}-O-\overset{X}{\underset{|}{CH}}-Y$$

where $R_7$ may be H, $CH_3$, or $CH_2CH_3$; $R_8$ is H or $CH_3$; $R_9$ is $CH_3$; Z is an alkyl group having from 1 to 3 carbon atoms.

Belgium Pat. No. 862,499 discloses a group of pyrethroidal esters which are characterized by the so-called "Pydrin alcohol" and a class of olefinic esters. The pesticidal phenoxy benzyl pentene carboxylates are prepared by esterifying a phenoxy benzyl alcohol with pentene carboxylic acid. According to the disclosure of Belgium Pat. No. 862,499, esters are prepared using a synthetic method from acids of the general formula III:

$$\text{III} \quad \underset{R_6\phantom{xx}H\phantom{xx}R_4}{\diagdown\!\!\diagup\phantom{x}|} \\ \phantom{xx}\underset{R_7}{\diagup}C=C\diagdown\overset{|}{\underset{|}{C}}\phantom{x}CH-CO_2H \\ \phantom{xxxxxxxxxxxx}\underset{R_2\phantom{xx}R_5}{\phantom{x}}$$

wherein
- $R_4$ = lower alkyl
- $R_2$ and $R_5$ = H or an alkyl group having from 1-4 carbon atoms
- $R_6$ and $R_7$ = Cl or Br.

Belgium Pat. No. 860,687 discloses phenoxybenzyl haloalkenoate esters which are useful as insecticides and acaricides and have the following structural formula IV:

$$\text{IV} \quad \underset{X\phantom{xx}H}{\diagdown\!\!\diagup} \\ \underset{Y}{\diagup}C=C\diagdown\underset{CH_2CHCO_2CH}{\overset{CH_3\phantom{x}R_1}{\underset{|}{\phantom{x}}\phantom{xx}\underset{|}{Z}}}-\!\!\!\bigcirc\!-O-\!\!\!\bigcirc$$

wherein X is halogen, Y is halogen or $CH_3$, Z is CN or ethynyl, and $R_1$ is H or $CH_3$.

BRIEF DESCRIPTION OF THE INVENTION

This invention relates to compounds corresponding to the following general formula V:

$$\text{V} \quad \underset{R_1\phantom{xx}R_3}{\diagdown\!\!\diagup} \\ \underset{R_2}{\diagup}C=C\diagdown\underset{R_4}{\overset{|}{\underset{|}{C}}}-\overset{R_6}{\underset{|}{CH}}-\overset{O}{\underset{\|}{C}}-O-R_7 \\ \phantom{xxxxxxxxxx}\underset{R_5}{\phantom{x}}$$

wherein:
- $R_1$, $R_2$, and $R_3$ are independently H, a lower alkyl group having from 1 to 3 carbon atoms or halogen;
- $R_4$ and $R_5$ are independently H, a lower alkyl group having from 1 to 3 carbon atoms, polyhaloalkyl, haloalkyl, halogen, a lower alkenyl group having from 2 to 3 carbon atoms, a lower cycloalkyl group having from 3 to 5 carbon atoms, a lower cycloalkenyl group having from 3 to 5 carbon atoms, cyano, nitro, a lower alkoxy group having from 1 to 3 carbon atoms, arloxy, a lower alkylthio group having from 1 to 3 carbon atoms, arylthio, a lower alkylsulfinyl group having from 1 to 3 carbon atoms, arylsulfinyl, a lower alkylsulfonyl group having from 1 to 3 carbon atoms, arylsulfonyl, acylamido, or a lower dialkylamino group having from 1 to 3 carbon atoms;
- $R_6$ is selected from the group consisting of: (1) cycloalkyl, alkenyl, branched alkenyl, or cycloalkenyl; or (2) a branched alkyl group having from 3 to 5 carbon atoms or an alkyl group having from 1 to 5 carbon atoms, with the proviso that $R_4$ or $R_5$ is other than hydrogen.
- $R_7$ is a member selected from the group consisting of:

-continued

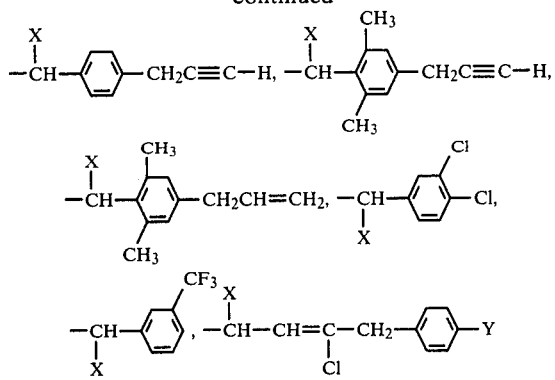

wherein:
X is hydrogen, cyano, ethynyl, thiamido, a lower alkyl group having from 1 to 3 carbon atoms, a lower cycloalkyl group having from 3 to 5 carbon atoms, a lower alkenyl group having from 2 to 5 carbon atoms, a lower cycloalkenyl group having from 3 to 5 carbon atoms or polyhaloalkyl;

Y is hydrogen, a lower alkyl group having from 1 to 3 carbon atoms, polyhaloalkyl, haloalkyl, halogen, cyano, nitro, a lower alkoxy group having from 1 to 3 carbon atoms, aryloxy, a lower alkylthio group having from 1 to 3 carbon atoms, arylthio, a lower alkylsulfinyl group having from 1–3 carbon atoms, arylsulfonyl, alkylsulfonyl, acylamido, or a lower dialkylamino group having from 1 to 3 carbon atoms;

$R_8$ is bromine or chlorine; and

Z is oxygen, sulfur or its oxides, or methylene.

Structure V is understood to include geometrical isomers about the $C_4$–$C_5$ bond and optical isomers at $C_2$.

These compounds generalized by structure V, with varying degrees of efficiency, are useful in combating insects and mites. In general, the compositions having the greatest degree of pesticidal activity are those in which only one of $R_4$ or $R_5$ is methyl. The preferred compositions of this invention are those in which $R_1$ and $R_2$ are halogen, preferably chlorine or bromine; wherein only one of $R_4$ or $R_5$ is methyl; and wherein $R_6$ is isopropyl or cyclopropyl.

It has been found that two halogens at the terminal end of the double bond ($R_1$ and $R_2$=halogen) provide pyrethroid esters having maximum activity. One or no halogens or methyl groups at the double bond terminus results in significantly lower biocidal activity. It has also been found that a halogen or methyl group at $C_4$ ($R_3$=halogen or methyl) results in a significant reduction in insecticidal activity. Maximum insecticidal activity is obtained when $R_3$=hydrogen.

Moreover, the insecticidal activity of the halo-4-alkenoic acid esters of this invention have been discovered to be critically dependent upon the substitution pattern at $C_3$, i.e., at $R_4$ and $R_5$. Table IV set forth subsequently herein illustrates that the variation in activity with substitution at $C_3$ can be seen to be in the order of $CH_3$->$H$>$CH_3CH_2$->gem- $(CH_3)_2$. Table IV also illustrates applicant's discovery that activity of halo-4-alkenoic acid esters on most insects may be remarkably enhanced with a single methyl substituent at $C_3$ ($R_4$ or $R_5$=$CH_3$). For example, when compared with a prior art halo-4-alkenoic acid esters having hydrogen substituents at $C_3$ such as disclosed in Belgium Pat. No. 860,687, an ester according to this invention which had a single methyl substituent at $C_3$ was found to be 10 times more active on the aphid and 8 times more active on the Mexican bean beetle.

The increase in activity with methyl substitution at $C_3$ in the halo-4-alkenoic acid esters of this invention is particularly surprising when compared to structure activity features observed with the alkenyl cyclopropanecarboxylates and the α-isopropyl acetates. See M. Elliot, *Synthesis Pyrethroids*, ACM Symposium Series 42, 1977, page 9. Pyrethroid esters of structure VI show a high level of broad spectrum insecticidal activity but methyl substitution at $C_3$ to give structure VII results in complete loss of activity.

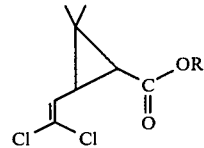

VI

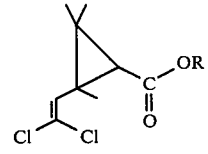

VII

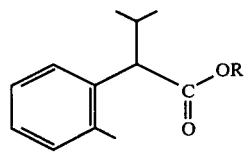

VIII

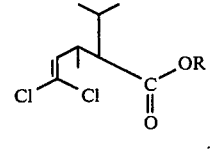

IX

Esters of α-isopropylphenylacetic acid also exhibit a high level of insecticidal activity, but ortho substituents on the aryl ring, as in structure VII, afford substantially reduced activity. The structural similarity of the active haloalkenoic acid ester of structure IX to the inactive compounds of structures VII and VIII provides a sharp contrast which further indicates the unexpected increased activity of applicant's pyrethroid esters. Also, when more than one methyl group is substituted at $C_3$, insecticidal activity has been found to decrease.

When a methyl group is present at $C_3$, the preferred substituent ($R_6$) at $C_2$ is a small substituent such as ethyl, cyclopropyl, isopropyl or the like. Isopropyl and cyclopropyl substituents at $C_2$ were found to be equivalent in activity on all insects tested except the armyworm. For worm activity, the preferred substituent at $C_2$ with a methyl group at $C_3$ is cyclopropyl>ethyl>isopropyl. The preferred substitution patterns at $C_2$ and $C_3$ have been found to be clearly related and cannot be viewed as isolated sites in any analysis of structure activity features. The degree of steric bulk at $C_2$ and $C_3$ is critical to the efficacy of the receptor site interaction for halo 4-alkenoic acid esters of this invention.

The esters according to this invention exhibit broad spectrum insecticidal and miticidal activity and are relatively safe to plants and mammals, i.e., low toxicity to mammals and little or no phytotoxicity.

The esters of this invention may be prepared by any of several methods which involve reacting an alcohol of the formula $R_7$-OH with an acid of the formula X:

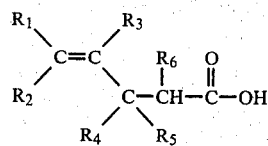
X or a reactive derivative thereof, wherein $R_1$–$R_7$ are as defined hereinabove for structure V. The term reactive derivative of the acid refers to an acid halide, an acid anhydride, an ester with an alcohol having a low boiling point, an alkali metal salt, a silver salt, or an organic tertiary amine base salt of the acid. In certain instances, the halide or sulfoxylate derived from the alcohol $R_7$—OH may be reacted with the acid derivative. These methods are illustrated by the general equations shown below:

Method 1

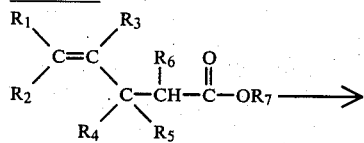

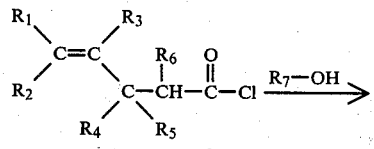

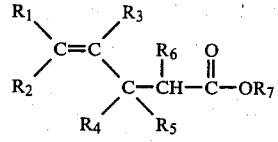

The acid halide is obtained by reacting the carboxylic acid with thionyl chloride, phosphorous trichloride, etc. The desired ester can be obtained in high yield by reacting the alcohol and the acid halide at room temperature using a proton acceptor, for example, an organic tertiary amine such as pyridine, triethylamine, and the like. The acid halides which can be used in the process of this invention may be acid fluorides, bromides, or chlorides, but an acid chloride is generally preferred. The presence of an inert solvent in the esterification reaction is not essential, but it is generally preferred to use an inert solvent to assure a smooth reaction in this step. Any solvent may be used which is inert to the reactants and the ester product. Preferred solvents include benzene, toluene, carbon tetrachloride, methylene chloride, chloroform, and the like.

Optionally, in method 1 the acid anhydride may be used in place of the acid halide.

Method 2

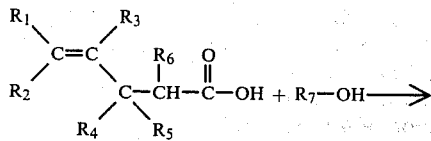

-continued

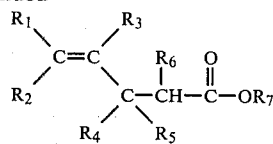

The esters of this invention may be prepared by reacting the carboxylic acids with the alcohols in an appropriate inert solvent at room temperature or an elevated temperature under an appropriate dehydrating condition, e.g. dicyclohexylcarbodiimide. Suitable solvents for this method are ether, toluene, benzene, carbon tetrachloride, methylene chloride, hexane, and the like.

Method 3

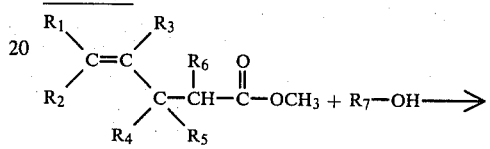

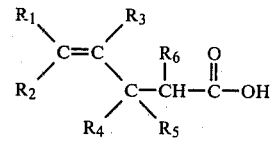

When the alcohol $R_7$-OH is stable to strong base, the desired esters may be obtained by refluxing a low boiling point alcohol ester of the acid in the presence of an appropriate organic base catalyst in an inert solvent while removing the low boiling alcohol liberated in the reaction by azeotropic distillation. The base should be the alkali metal alkoxide corresponding to the low boiling alcohol of the ester used or an alkali metal hydride, e.g. sodium or lithium hydride. Preferred solvents for this method are toluene or benzene.

When a halide or sulfoxylate of the alcohol $R_7$-OH is used, the carboxylic acid is generally employed in the form of an alkali metal salt, a silver salt, or an organic tertiary amine base salt. These salts may be formed in situ by adding simultaneously the carboxylic acid and the corresponding base to the reaction system. In this case, a solvent such as toluene, benzene, acetone, dimethylsulfoxide, dimethylformamide, and the like is preferred, and the reaction is preferably conducted by heating the reaction mixture at or below the boiling point of the solvent used. Methods 4 and 5 below are illustrative of the processes described above.

Method 4

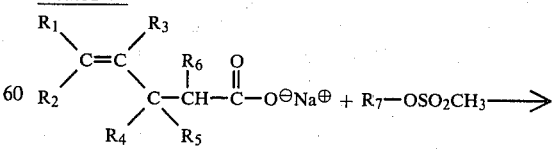

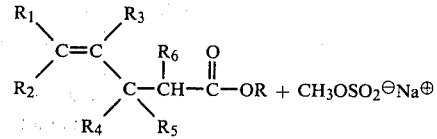

Method 5

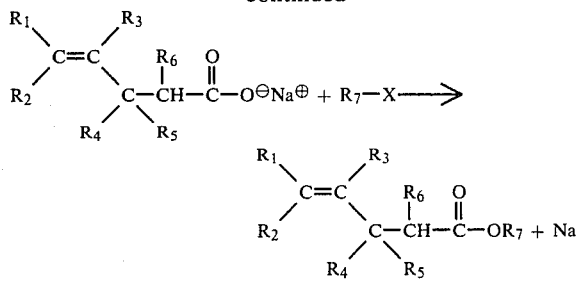

An especially active series of esters are those prepared from α-cyano-m-phenoxybenzyl alcohol. These esters can be conveniently prepared as shown in method 6.

Method 6

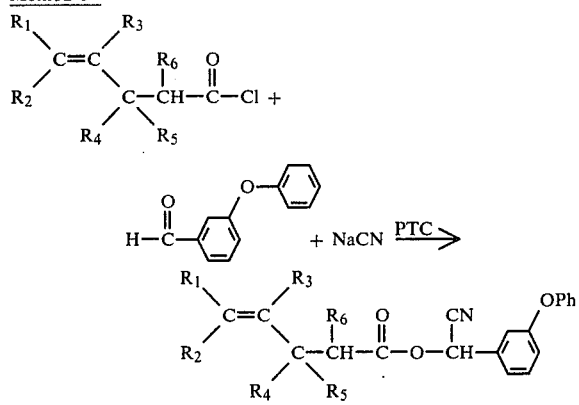

The process illustrated as Method 6 above utilizes from 1.0 to 1.1 molar equivalents of the m-phenoxybenzaldehyde, 1.0 molar equivalents of the acid chloride, and 1.5 to 1.1 molar equivalents of sodium cyanide. The phase transfer catalyst is employed in 0.10-0.01 molar equivalent amounts. In general, larger quantities of the PTC result in shorter reaction times.

Suitable phase transfer catalysts for method 6 are methyltricaprylammonium chloride, benzyltriethylammonium, chloride, hexadecyltributylphosphonium bromide, tetra-n-butylammonium hydrogen sulfate, tetra-n-butylammonium chloride, trioctylpropylammonium chloride, and the like.

Method 6 is neither temperature nor pressure sensitive and may be run over a wide range of these variables. A preferred reaction condition is room temperature and autogenous pressure.

The carboxylic acids used to prepare the esters of this invention are synthesized by several methods which are described in detail in my U.S. Patent application filed July 2, 1979, entitled "Novel Halo-4-Alkenoic Acids and Their Use as Pesticidal Intermediates", the disclosure of which is incorporated herein by reference. The alcohols used to prepare the esters of this invention are all known compounds whose preparation is described in the chemical literature. See *Synthetic Pyrethroida,* Elliot, M. ed., ACS Symposium Series 42, American Chemical Society, Washington, D.C. 1977 and references cited therein.

The following specific examples are presented to more particularly illustrate the manner in which the compounds of this invention may be prepared:

EXAMPLES

EXAMPLE I (α-cyano-m-phenoxybenzyl)5,5-dichloro-3-methyl-2-isopropyl-4-pentenoate A 100 ml R.B. flask was equipped with a magnetic stirrer, dropping funnel, and $N_2$ inlet. The flask was dried with external heat, then charged with 30 ml of carbon tetrachloride, 7.0 g (0.03 mol) of 5,5-dichloro-3-methyl-2-isopropyl-4-pentenoic acid and four drops of pyridine. The reaction mixture was cooled in an ice bath, and 7.14 g (0.06 mol) of thionyl chloride was added dropwise over a 15 minute period. The reaction mixture was then warmed to reflux for 1½ hrs. The reaction mixture was cooled to room temperature and excess thionyl chloride and carbon tetrachloride was removed on the rotary evaporator. The residue was taken up in 30 ml of carbon tetrachloride and cooled under $N_2$ in an ice bath. To the reaction mixture was added a solution of 7.5 g (0.033 mol) of α-cyano-m-phenoxybenzyl alcohol, 2.93 g (0.037 mol) of pyridine and 10 ml of carbon tetrachloride. The reaction mixture was stirred for 1 hr at 0° C., then overnight at room temperature. The reaction mixture was then diluted with 150 ml of $CH_2Cl_2$, 25 ml of water added, and the layers separated. The organic layer was washed with 5% HCl (2×50 ml), 10% $Na_2CO_3$ (2×50 ml), and water (1×50 ml). The organic layer was dried ($MgSO_4$), and the solvent removed to leave 10.2 g of a yellow oil.

This oil was purified by low pressure liquid chromatography using a pre-packed EM silica gel column and eluting with 500 ml of hexane, 500 ml of 99:1 hexane-ethyl acetate, 500 ml of 97:3 hexane-ethyl acetate, and 1000 ml of 95:5 hexane-ethyl acetate. The eluent was collected in 10 ml fractions, and all fractions showing a single spot at Rf=0.49 (70:30 hexane-ethyl acetate) were combined and the solvent removed to leave 4.9 g of a clear, colorless oil (38% yield) which IR and NMR showed to be the desired product.

| Anal. | % C | % H | % N |
|---|---|---|---|
| Calcd. | 63.89 | 5.36 | 3.24 |
| Found | 63.56 | 5.43 | 3.12 |

EXAMPLE II (α-cyano-m-phenoxybenzyl)5,5-dichloro-3-methyl-2-cyclopropyl-4-pentenoate A 100 ml R.B. flask was equipped with a magnetic stirrer, dropping funnel, and $N_2$ inlet. The flask was dried with external heat, then charged with 30 ml of carbon tetrachloride, 4.0 g (0.0178 mol) of 5,5-dichloro-3-methyl-2-cyclopropyl-4-pentenoic acid, and four drops of pyridine. The reaction mixture was cooled in an ice bath, and 5.34 g (0.0534) mol) of thionyl chloride as added dropwise over a 15 minute period. The reaction mixture was then warmed to reflux for 1½ hrs. The reaction mixture was cooled to room temperature and excess thionyl chloride and carbon tetrachloride was removed on the rotary evaporator. The residue was taken up in 30 ml of carbon tetrachloride and cooled under $N_2$ in an ice bath. To the reaction mixture was added a solution of 4.18 g (0.0178 mol) of α-cyano-m- phenoxybenzyl alcohol, 1.55 g (0.0196 mol) of pyridine and 10 ml of carbon tetrachloride. The reaction mixture was stirred for 1 hr at 0° C., then overnight at room temperature. The reaction mixture was then diluted with 150 ml of $CH_2Cl_2$, 25 ml of water added, and the layers separated. The organic layer was washed with 5% HCl (2×50 ml), 10% $Na_2CO_3$ (2×50 ml), and water (1×50 ml). The organic layer as dried ($MgSO_4$), and the solvent removed to leave 6.9 g of a yellow oil.

This oil was purified by low pressure liquid chromatography using a pre-packed EM silica gel column and eluting with 500 ml of hexane, 500 ml of 99:1 hexane-ethyl acetate, 500 ml of 97:3 hexane-ethyl acetate, and 1000 ml of 95:5 hexane-ethyl acetate. The eluent was collected in 10 ml fractions, and all fractions showing a single spot at Rf=0.42 (70:30 hexane-ethyl acetate) were combined and the solvent removed to leave 3.5 of a clear, colorless oil (46% yield) which IR and NMR showed to be the desired product.

| Anal. | % C | % H | % N |
| --- | --- | --- | --- |
| Calcd. | 64.20 | 4.92 | 3.25 |
| Found | 64.30 | 4.95 | 3.19 |

All of the compounds whose physical properties are summarized in Table I discussed subsequently herein were prepared using the general procedure given in Examples I and II.

The following novel halo-4-alkenoic acid esters disclosed herein in addition to those described in Examples I-II are illustrative of the new composition of this invention:

[3-(2,2-dichlorovinyloxy)-α-cyanobenzyl]5,5-dichloro-3-methyl-2-isopropyl-4-pentenoate
[3-(2,2-dichlorovinyloxy)-α-cyanobenzyl]5,5-dichloro-3-trifluoromethyl]-2-isopropyl-4-pentenoate
3-(2,2-dichlorovinyloxy)-α-cyanobenzyl]5,5-dichloro-3,3-dimethyl-2-isopropyl-4-pentenoate
(α-cyano-m-phenoxybenzyl)5,5-dichloro-3-trifluoromethyl-2-isopropyl-4-pentenoate (α-cyano-m-phenoxybenzyl)5,5-dichloro-3,3-dimethyl-2-isopropyl-4-pentenoate (α-cyano-m-phenoxybenzyl)5,5-dichloro-3-ethyl-2-isopropyl-4-pentenoate
(α-cyano-m-phenoxybenzyl)5,5-dichloro-2,3-diisopropyl-4-pentenoate
(α-cyano-m-phenoxybenzyl)5,5-dichloro-3-tert-butyl-2-isopropyl-4-pentenoate
(α-cyano-m-phenoxybenzyl)5-chloro-3-methyl-2-isopropyl-4-hexenoate
(α-cyano-m-phenoxybenzyl)5-chloro-3,3-dimethyl-2-isopropyl-4-hexenoate
(α-cyano-m-phenoxybenzyl)5-chloro-3-trifluoromethyl-2-isopropyl-4-hexenoate
(α-cyano-m-phenoxybenzyl)5-chloro-3-methyl-2-isopropyl-4-pentenoate
(α-cyano-m-phenoxybenzyl)5-chloro-3,3-dimethyl-2-isopropyl-4-pentenoate
(α-cyano-m-phenoxybenzyl)5-chloro-3-trifluoromethyl-2-isopropyl-4-pentenoate
(α-cyano-m-phenoxybenzyl)5-chloro-2,3-diisopropyl-4-hexenoate
(α-cyano-m-phenoxybenzyl)5-chloro-2,3-diisopropyl-4-pentenoate
[3-(2,2-dichlorovinyloxy)-α-cyanobenzyl]5-chloro-3-methyl-2-isopropyl-4-hexenoate
[3-(2,2-dichlorovinyloxy)-α-cyanobenzyl]5-chloro-3-methyl-2-isopropyl-4-pentenoate
[3-(2,2-dichlorovinyloxy)-α-cyanobenzyl]5-chloro-3,3-dimethyl-2-isopropyl-4-hexenoate
[3-(2,2-dichlorovinyloxy)-α-cyanobenzyl]5-chloro-3,3-dimethyl-2-isopropyl-4-pentenoate
(α-ethynyl-m-phenoxybenzyl)5,5-dichloro-3-methyl-2-isopropyl-4-pentenoate
(α-ethynyl-m-phenoxybenzyl)5,5-dichloro-3trifluoromethyl-2-isopropyl-4-pentenoate
(α-ethynyl-m-phenoxybenzyl)5,5-dichloro-3,3-dimethyl-2-isopropyl-4-pentenoate
(α-ethynyl-m-phenoxybenzyl)5-chloro-3-methyl-2-isopropyl-4-hexenoate
(α-ethynyl-m-phenoxybenzyl)5-chloro-3-methyl-2-isopropyl-4-pentenoate
(α-ethynyl-m-phenoxybenzyl)5-chloro-3,3-dimethyl-2-isopropyl-4-hexenoate
(α-ethynyl-m-phenoxybenzyl)5-chloro-3-trifluoromethyl-2-isopropyl-4-pentenoate
(α-ethynyl-m-phenoxybenzyl)5-chloro-3-trifluoromethyl-4-hexenoate
(α-ethynyl-m-phenoxybenzyl)5-chloro-2,3-diisopropyl-4-pentenoate (α-ethynyl-m-phenoxybenzyl)5-chloro-2,3-diisopropyl-4-hexenoate
(α-thioamido-m-phenoxybenzyl)5,5-dichloro-3-methyl-2-isopropyl-4-pentenoate
(α-thioamido-m-phenoxybenzyl)5,5-dichloro-3-trifluoromethyl-2-isopropyl-4-pentenoate
(α-thioamido-m-phenoxybenzyl)5,5-dichloro-3,3-dimethyl-2-isopropyl-4-pentenoate
(α-thioamido-m-phenoxybenzyl)5,5-dichloro-2,3-diisopropyl-4-pentenoate
(α-thioamido-m-phenoxybenzyl)5-chloro-3-methyl-2-isopropyl-4-pentenoate
(α-thioamido-m-phenoxybenzyl)5-chloro-3-trifluoromethyl-2-isopropyl-4-pentenoate
(α-thioamido-m-phenoxybenzyl)5-chloro-3,3-dimethyl-2-isopropyl-4-pentenoate
(α-thioamido-m-phenoxybenzyl)5-chloro-2,3-diisopropyl-4-pentenoate
(α-thioamido-m-phenoxybenzyl)5-chloro-3-methyl-2-isopropyl-4-hexenoate
(α-thioamido-m-phenoxybenzyl)5-chloro-3-trifluoromethyl-2-isopropyl-4-hexenoate
(α-thioamido-m-phenoxybenzyl)5-chloro-3,3-dimethyl-2-isopropyl-4-hexenoate
(α-thioamido-m-phenoxybenzyl)5-chloro-2,3-diisopropyl-4-hexenoate
(α-methyl-m-phenoxybenzyl)5,5-dichloro-3-methyl-2-isopropyl-4-pentenoate
(α-ethyl-m-phenoxybenzyl)5,5-dichloro-3-methyl-2-isopropyl-4-pentenoate
(α-n-propyl-m-phenoxybenzyl)5,5-dichloro-3-methyl-2-isopropyl-4-pentenoate
(α-isopropyl-m-phenoxybenzyl)5,5-dichloro-3-methyl-2-isopropyl-4-pentenoate
(α-cyclopropyl-m-phenoxybenzyl)5,5-dichloro-3-methyl-2-isopropyl-4-pentenoate
(α-cyclobutyl-m-phenoxybenzyl)5,5-dichloro-3-methyl-2-isopropyl-4-pentenoate
(α-cyclopentyl-m-phenoxybenzyl)5,5-dichloro-3-methyl-2-isopropyl-4-pentenoate
(α-ethenyl-m-phenoxybenzyl)5,5-dichloro-3-methyl-2-isopropyl-4-pentenoate
(α-allyl-m-phenoxybenzyl)5,5-dichloro-3-methyl-4-pentenoate (α-isopropenyl-m-phenoxybenzyl)5,5-dichloro-3-methyl-2-isopropyl-4-pentenoate
[α-(2-cyclobutenyl)-m-phenoxybenzyl]5,5-dichloro-3-methyl-2-isopropyl-4-pentenoate
[α-(2-cyclopentenyl)-m-phenoxybenzyl]5,5-dichloro-3-methyl-2-isopropyl-4-pentenoate
(α-trifluoromethyl-m-phenoxybenzyl)5,5-dichloro-3-methyl-2-isopropyl-4-pentenoate
[α-cyano-m-(4-fluorophenoxy)benzyl]5,5-dichloro-3-methyl-2-isopropyl-4-pentenoate
[α-cyano-m-(4-methylphenoxy)benzyl]5,5-dichloro-3-methyl-2-isopropyl-4-pentenoate
[α-cyano-m-(4-trifluoromethylphenoxy)benzyl]5,5-dichloro-3-methyl-2-isopropyl-4-pentenoate
[α-cyano-m-(4-methoxyphenoxy)benzyl]5,5-dichloro-3-methyl-2-isopropyl-4-pentenoate
[α-cyano-m-(4-cyanophenoxy)benzyl]5,5-dichloro-3-methyl-2-isopropyl-4-pentenoate
[α-cyano-m-(4-nitrophenoxy)benzyl]5,5-dichloro-3-methyl-2-isopropyl-4-pentenoate
[α-cyano-m-(4-phenoxyphenoxy)benzyl]5,5-dichloro-3-methyl-2-isopropyl-4-pentenoate
[α-cyano-m-(4-methylthiophenoxy)benzyl]5,5-dichloro-3-methyl-2-isopropyl-4-pentenoate
[α-cyano-m-(4-methylsulfinylphenoxy)benzyl]5,5-dichloro-3-methyl-2-isopropyl-4-pentenoate
[α-cyano-m-(4-methylsulfonylphenoxy)benzyl]5,5-dichloro-3-methyl-2-isopropyl-4-pentenoate
[α-cyano-m-(4-acetamidophenoxy)benzyl]5,5-dichloro-3-methyl-2-isopropyl-4-pentenoate
[α-cyano-m-(4-dimethylaminophenoxy)benzyl]5,5-dichloro-3-methyl-2-isopropyl-4-pentenoate
(m-phenoxybenzyl)5,5-dichloro-3-methyl-4-pentenoate
(m-phenoxybenzyl)5,5-dichloro-3,3-dimethyl-4-pentenoate
(m-phenoxybenzyl)5,5-dichloro-3-trifluoromethyl-4-pentenoate
(m-phenoxybenzyl)5,5-dichloro-2,3-diisopropyl-4-pentenoate
(5-benzyl-3-furylmethyl)5,5-dichloro-3-methyl-2-isopropyl-4-pentenoate
(5-benzyl-3-furylmethyl)5,5-dichloro-3,3-dimethyl-2-isorpopyl-4-pentenoate
(5-benzyl-3-furylmethyl)5,5-dichloro-3-trifluoromethyl-2-isopropyl-4-pentenoate
)5-benzyl-3-thiophenemethyl)5,5-dichloro-3-methyl-2-isopropyl-4-pentenoate
(5-benzyl-3-thiophenemethyl)5,5-dichloro-3,3-dimethyl-2-isopropyl-4-pentenoate
(5-benzyl-3-thiophenemethyl)5,5-dichloro-3-trifluoromethyl-2-isopropyl-4-pentenoate
(3,4,5,6-tetrahydrophthalimidomethyl)5,5-dichloro-2-isopropyl-3-methyl-4-pentenoate
(3,4,5,6-tetrahydrophthalimidomethyl)5,5-dichloro-3-trifluoromethyl-2-isopropyl-4-pentenoate
(3,4,5,6-tetrahydrophthalimidomethyl)5,5-dichloro-3,3-dimethyl-2-isopropyl-4-pentenoate
[m-(2-thipheneoxy)benzyl]5,5-dichloro-2-isopropyl-3-methyl-4-pentenoate
[m-(2-thipheneoxy)benzyl]5,5-dichloro-3,3-dimethyl-2-isopropyl-4-pentenoate
[m-(2-thipheneoxy)benzyl]5,5-dichloro-3-trifluoromethyl-2-isopropyl-4-pentenoate
(4-propargylbenzyl)5,5-dichloro-3-methyl-2-isopropyl-4-pentenoate
(4-propargylbenzyl)5,5-dichloro-3,3-dimethyl-2-isopropyl-4-pentenoate
(4-propargylbenzyl)5,5-dichloro-3-trifluoromethyl-2-isopropyl-4-pentenoate
(α-cyano-m-benzylbenzyl)-5,5-dichloro-3-methyl-2-isopropyl-4-pentenoate
(α-cyano-m-benzylbenzyl)5,5-dichloro-3,3-dimethyl-2-isopropyl-4-pentenoate
(α-cyano-m-benzylbenzyl)5,5-dichloro-3-trifluoromethyl-2-isopropyl-4-pentenoate
(2,6-dimethyl-4-propargylbenzyl)5,5-dichloro-2-isopropyl-3-methyl-4-pentenoate
(2,6-dimethyl-4-propargylbenzyl)5,5-dichloro-3,3-dimethyl-2-isopropyl-4-pentenoate
(2,6-dimethyl-4-proparglybenzyl)5,5-dichloro-3-trifluoromethyl-2-isopropyl-4-pentenoate
(2,6-dimethyl-4-allylbenzyl)5,5-dichloro-3-methyl-2-isopropyl-4-pentenoate
(2,6-dimethyl-4-allylbenzyl)5,5-dichloro-3-trifluoromethyl-2-isopropyl-4-pentenoate
(α-cyano-3,4-dichlorobenzyl)5,5-dichloro-3-methyl-2-isopropyl-4-pentenoate
(α-cyano-3,4-dichlorobenzyl)5,5-dichloro-3,3-dimethyl-2-isopropyl-4-pentenoate
(α-cyano-3,4-dichlorobenzyl)5,5-dichloro-3-trifluoromethyl-2-isopropyl-4-pentenoate
(α-cyano-m-trifluoromethyl)5,5-dichloro-3-methyl-2-isopropyl-4-pentenoate
(α-cyano-m-trifluoromethyl)5,5-dichloro-3,3-dimethyl-2-isopropyl-4-pentenoate
[3-chloro-4-(p-chlorophenyl)-2-butenyl]5,5-dichloro-3-methyl-2-isopropyl-4-pentenoate
[3-chloro-4-(p-chlorophenyl)-2-butenyl]5,5-dichloro-3,3-dimthyl-2-isopropyl-4-pentenoate
[3-chloro-4-(p-chlorophenyl)2-butenyl]5,5-dichloro-3-trifluoromethyl-2-isopropyl-4-pentenoate
(α-cyano-m-phenoxybenzyl)5,5-dichloro-3-methyl-2-cyclopropyl-4-pentenoate
(α-cyano-m-phenoxybenzyl)5,5-dichloro-3-methyl-2-tert-butyl-4-pentenoate
(α-cyano-m-phenoxybenzyl)5,5-dichloro-3-methyl-2-isopropenyl-4-pentenoate
(α-cyano-m-phenoxybenzyl)5,5-dichloro-3-methyl-2-secbutyl-4-pentenoate
(α-cyano-m-phenoxybenzyl)5,5-dichloro-3-methyl-2-isobutyl-4-pentenoate
(α-cyano-m-phenoxybenzyl)5,5-dichloro-3-methyl-2-(1-cyclobutenyl)-4-pentenoate
(α-cyano-m-phenoxybenzyl)5,5-dichloro-3-methyl-2-isopentyl-4-pentenoate
(α-cyano-m-phenoxybenzyl)5,5-dichloro-3-methyl-2-(2-cyclopentenyl)-4-pentenoate
(α-cyano-m-phenoxybenzyl)5,5-difluoro-3-methyl-2-isopropyl-4-pentenoate
(α-cyano-m-phenoxybenzyl)5,5-difluoro-3-trifluoromethyl-2-isopropyl-4-pentenoate
(α-cyano-m-phenoxybenzyl)5,5-difluoro-3,3-dimethyl-2-isopropyl-4-pentenoate
(α-cyano-m-phenoxybenzyl)5,5-dibromo-3-methyl-2-isopropyl-4-pentenoate
(α-cyano-m-phenoxybenzyl)5,5-dibromo-3-trifluoromethyl-2-isopropyl-4-pentenoate
(α-cyano-m-phenoxybenzyl)5,5-dibromo-3,3-dimethyl-2-isopropyl-4-pentenoate
(α-cyano-m-phenoxybenzyl)5,5-dichloro-3-cyano-2-isopropyl-4-pentenoate
(α-cyano-m-phenoxybenzyl)3,3,5,5-tetrachloro-2-isopropyl-4-pentenoate
(α-cyano-m-phenoxybenzyl)5,5-dichloro-3-nitro-2-isopropyl-4-pentenoate (α-cyano-m-phenoxybenzyl)5,5-dichloro-3-methoxy-2-isopropyl-4-pentenoate (α-cyano-m-phenoxybenzyl)5,5-dichloro-3-phenoxy-2-isopropyl-4-pentenoate (α-cyano-m-phenoxybenzyl)5,5-dichloro-3-methylsulfenyl-2-isopropyl-4-pentenoate (α-cyano-m-phenoxybenzyl)5,5-dichloro-3-methylsulfinyl-2-isopropyl-4-pentenoate (α-cyano-m-phenoxybenzyl)5,5-dichloro-3-methylsulfonyl-2-isopropyl-4-pentenoate (α-cyano-m-phenoxybenzyl)5,5-dichloro-3-acetamido-2-isopropyl-4-pentenoate (α-cyano-m-phenoxybenzyl)5,5-dichloro-3-dimethylamino-2-isopropyl-4-pentenoate Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The concentrations in part per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae Scop.*) reared on potted dwarf nasturtium plants at 65°–70° F. and 50–70 percent relative humidity, constituted with test insects. For testing purposes, the number of aphids per pot was standardized to 100–150 by trimming plants containing excess aphids.

The test compounds were formulated by diluting the stock suspension with water to give a suspension containing 500 parts of test compund per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Spodoptera eridania*, (Cram.)), reared on Tendergreen bean plants at a temperature of 80°±5° F. and a relative humidity of 50± percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were spearated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temprature of 80°±5° F. and 50±5 percent relative humidity, were the test insects.

The test compounds were formulated by diluting the stock suspension with water to give a suspension containing 500 parts of test compound per million parts of final formulation.

Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F, for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243–244, 261) under controlled conditions of 80°±° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absobent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and nymphal stage of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty hour hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds against aphid, mite, Southern Armyworm, Bean Beetle and house fly was rated as follows:
A = excellent control
B = partial control
C = no control
Dashes indicate no test conducted.

TABLE I

Insecticidal Activity of Esters of Halo-4-Alkenoic Acids
(at 500 ppm, A = complete kill; B = some kill; C = no kill)

| Example | Structure | Aphid | Mite | SAW | MBB | HF |
|---------|-----------|-------|------|-----|-----|-----|
| IV | Cl₂C=CH-CH(CH₃)-CH(CH(CH₃)₂)-CO₂CH(CN)-C₆H₄-O-C₆H₅ | A | A | A | A | A |
| V | Cl₂C=CH-CH₂-CH(CH(CH₃)₂)-CO₂CH(CN)-C₆H₄-O-CH=CCl₂ | A | B | A | A | A |
| VI | Br₂C=CH-CH₂-CH(CH(CH₃)₂)-CO₂CH(CN)-C₆H₄-O-CH=CCl₂ | A | B | A | A | A |
| VII | Cl₂C=CH-CH₂-CH(CH(CH₃)₂)-CO₂CH₂-(furyl)-CH₂-C₆H₅ | A | B | A | A | A |
| VIII | Br₂C=CH-CH₂-CH(CH(CH₃)₂)-CO₂CH₂-(furyl)-CH₂-C₆H₅ | A | B | A | A | A |

TABLE I-continued

Insecticidal Activity of Esters of Halo-4-Alkenoic Acids
(at 500 ppm, A = complete kill; B = some kill; C = no kill)

| Example | Structure | Aphid | Mite | SAW | MBB | HF |
|---|---|---|---|---|---|---|
| IX | (H,H)C=C(H,Cl)–CH₂CH(CH(CH₃)₂)CO₂CH(CN)–C₆H₄–O–C₆H₅ | A | A | A | A | B |
| X | (H,H)C=C(H,Cl)–CH₂CH(CH₂CH₃)CO₂CH₂–C₆H₄–O–C₆H₅ | A | C | C | C | C |
| XI | (H,H)C=C(H,Br)–CH₂CH(CH(CH₃)₂)CO₂CH(CN)–C₆H₄–O–C₆H₅ | A | C | B | A | B |
| XII | (Cl,H)C=C(H,H)–CH₂CH(CH(CH₃)₂)CO₂CH(CN)–C₆H₄–O–C₆H₅ | A | A | A | A | B |
| XIII | (H,Cl)C=C(H,Cl)–CH₂CH(CH(CH₃)₂)CO₂CH(CN)–C₆H₄–O–C₆H₅ | A | A | B | A | C |
| XIV | (Cl,H)C=C(H,Cl)–CH₂CH(CH(CH₃)₂)CO₂CH(CN)–C₆H₄–O–C₆H₅ | A | A | B | A | C |
| XV | (Cl,Cl)C=C(H,Cl)–CH₂CH(CH(CH₃)₂)CO₂CH(CN)–C₆H₄–O–C₆H₅ | C | C | B | B | C |
| XVI | (Cl,Cl)C=C(CH₃,H)–CH₂CH(CH(CH₃)₂)CO₂CH(CN)–C₆H₄–O–C₆H₅ | C | C | B | A | C |
| XVII | (Cl,Cl)C=C(H,H)–CH₂CH(cyclopropyl)CO₂CH(CN)–C₆H₄–O–C₆H₅ | A | B | C | B | C |
| XVIII | (Cl,Cl)C=C(H,H)–CH(CH₃)–CH(cyclopropyl)CO₂CH(CN)–C₆H₄–O–C₆H₅ | A | A | A | A | A |
| XIX | (Cl,Cl)C=C(H,H)–CH(CH₂CH₃)–CH(CH(CH₃)₂)CO₂CH(CN)–C₆H₄–O–C₆H₅ | A | A | B | A | C |
| XX | (Cl,Cl)C=C(H,H)–C(CH₃)(CH₃)–CH(CH(CH₃)₂)CO₂CH(CN)–C₆H₄–O–C₆H₅ | B | C | C | C | C |

TABLE I-continued

Insecticidal Activity of Esters of Halo-4-Alkenoic Acids
(at 500 ppm, A = complete kill; B = some kill; C = no kill)

| Example | Structure | Aphid | Mite | SAW | MBB | HF |
|---|---|---|---|---|---|---|
| XXI | Cl₂C=CH-CH(CH₃)-CH(CH₃)-CO₂-CH(CN)-(3-phenoxyphenyl) | A | C | B | A | C |
| XXII | Cl₂C=CH-CH(CH₃)-CH(CH₂CH₃)-CO₂-CH(CN)-(3-phenoxyphenyl) | A | A | A | A | A |
| XXIII | Cl₂C=CH-C(CH₃)₂-CH(CH₂CH₃)-CO₂-CH(CN)-(3-phenoxyphenyl) | B | C | C | B | C |
| XXIV | Cl₂C=CH-CH(CH₃)-CH(cyclopentyl)-CO₂-CH(CN)-(3-phenoxyphenyl) | A | B | C | C | C |
| XXV | Cl₂C=CH-CH(CH₃)-CH(iPr)-CO₂-CH(CN)-(3-(4-chlorophenoxy)phenyl) | A | A | A | A | A |
| XXVI | Cl₂C=CH-CH(CH₃)-CH(cyclopropyl)-CO₂-CH(CN)-(3-(4-fluorophenoxy)phenyl) | A | A | A | A | A |
| XXVII | Cl₂C=CH-CH(CH₃)-CH(iPr)-CO₂-CH(CN)-(3-(4-fluorophenoxy)phenyl) | A | A | A | A | A |
| XXVIII | Cl₂C=CH-CH(CH₃)-CH(cyclopropyl)-CO₂-CH(CN)-(3-(4-chlorophenoxy)phenyl) | A | A | B | A | A |
| XXIX | Cl₂C=CH-CH(CH₃)-CH(iPr)-CO₂-CH(CN)-(3-(4-methylphenoxy)phenyl) | A | A | C | A | B |
| XXX | Cl₂C=CH-CH(CH₃)-CH(cyclopropyl)-CO₂-CH(CN)-(3-(4-methylphenoxy)phenyl) | A | A | C | A | C |
| XXXI | Cl₂C=CH-CH(CH₃)-CH(iPr)-CO₂-CH(CN)-(3-(4-methoxyphenoxy)phenyl) | A | C | B | A | A |

TABLE I-continued

Insecticidal Activity of Esters of Halo-4-Alkenoic Acids
(at 500 ppm, A = complete kill; B = some kill; C = no kill)

| Example | Structure | Aphid | Mite | SAW | MBB | HF |
|---|---|---|---|---|---|---|
| XXXII | Cl₂C=CH-CH(CH₃)-cyclopropyl-CHCO₂CH(CN)-C₆H₄-O-C₆H₄-OCH₃ | A | A | C | A | A |
| XXXIII | Cl₂C=C(CH₃)-C(CH₃)-cyclopropyl-CHCO₂CH(CN)-C₆H₄-O-C₆H₅ | A | C | B | A | C |
| XXXIV | Cl₂C=CH-CH(CH₃)-cyclopropyl-CHCO₂CH(C≡CH)-C₆H₄-O-C₆H₅ | A | A | A | A | A |
| XXXV | Cl₂C=CH-CH(CH₃)-cyclopropyl-CHCO₂CH(C≡CH)-C₆H₄-O-C₆H₅ | A | A | A | A | A |

TABLE II:

Elemental Analysis

| Example | Molecular Formula | Calculated C | Calculated H | Calculated N | Found C | Found H | Found N |
|---|---|---|---|---|---|---|---|
| IV | C₂₃H₂₃Cl₂NO₃ | 63.89 | 5.36 | 3.24 | 63.56 | 5.43 | 3.12 |
| V | C₁₈H₁₇Cl₄NO₃ | 49.46 | 3.92 | 3.20 | 49.52 | 3.69 | 3.16 |
| VI | C₁₈H₁₇Br₂Cl₂NO₃ | 41.08 | 3.26 | 2.66 | 40.96 | 3.11 | 2.67 |
| VII | C₂₀H₂₂Cl₂O₃ | 63.34 | 5.31 | — | 63.14 | 5.62 | — |
| VIII | C₂₀H₂₂Br₂O₃ | 51.31 | 4.31 | — | 51.22 | 4.60 | — |
| IX | C₂₂H₂₂ClNO₃ | 68.83 | 5.78 | 3.65 | 69.29 | 5.58 | 3.64 |
| X | C₂₁H₂₀ClNO₃ | 68.20 | 5.45 | 3.79 | 69.04 | 5.25 | 3.85 |
| XI | C₂₂H₂₂BrNO₃ | 61.68 | 5.18 | 3.27 | 62.27 | 4.85 | 3.37 |
| XII | C₂₂H₂₂ClNO₃ | 68.84 | 5.78 | 3.65 | 69.29 | 5.62 | 3.66 |
| XIII | C₂₂H₂₁Cl₂NO₃ | 63.17 | 5.06 | 3.35 | 63.44 | 5.08 | 3.60 |
| XIV | C₂₂H₂₁Cl₂NO₃ | 63.17 | 5.06 | 3.35 | 63.58 | 5.17 | 3.40 |
| XV | C₂₂H₂₀Cl₃NO₃ | 58.36 | 4.45 | 3.09 | 58.51 | 4.68 | 3.11 |
| XVI | C₂₃H₂₃Cl₂NO₃ | 63.89 | 5.36 | 3.24 | 64.36 | 5.41 | 3.11 |
| XVII | C₂₂H₁₉Cl₂NO₃ | 63.47 | 4.60 | 3.36 | 63.79 | 4.51 | 3.35 |
| XVIII | C₂₃H₂₁Cl₂NO₃ | 64.20 | 4.92 | 3.25 | 64.30 | 4.95 | 3.19 |
| XIX | C₂₄H₂₅Cl₂NO₃ | 64.58 | 5.65 | 3.14 | 64.91 | 5.66 | 3.05 |
| X | C₂₄H₂₅Cl₂NO₃ | 64.58 | 5.65 | 3.14 | 64.87 | 5.69 | 3.19 |
| XXI | C₂₁H₁₉Cl₂NO₃ | 62.39 | 4.74 | 3.47 | 62.66 | 4.66 | 3.39 |
| XXII | C₂₂H₂₁Cl₂NO₃ | 63.17 | 5.06 | 3.35 | 63.34 | 4.93 | 3.30 |
| XXIII | C₂₃H₂₃Cl₂NO₃ | 63.89 | 5.36 | 3.24 | 64.47 | 5.32 | 3.23 |
| XXIV | C₂₅H₂₅Cl₂NO₃ | 65.51 | 5.50 | 3.06 | 65.73 | 5.38 | 3.01 |
| XXV | C₂₃H₂₃Cl₃NO₃ | 59.18 | 4.75 | 3.00 | 59.44 | 4.70 | 3.00 |
| XXVI | C₂₃H₂₀Cl₂FNO₃ | 61.34 | 4.92 | 3.11 | 62.11 | 4.39 | 3.10 |
| XXVII | C₂₃H₂₂Cl₂FNO₃ | 61.34 | 4.92 | 3.11 | 61.71 | 4.85 | 2.53 |
| XXVIII | C₂₃H₂₀Cl₃NO₃ | 59.44 | 4.34 | 3.01 | 59.64 | 4.29 | 3.06 |
| XXIX | C₂₄H₂₅Cl₂NO₃ | 64.58 | 5.65 | 3.14 | 64.95 | 5.52 | 3.10 |
| XXX | C₂₄H₂₃Cl₂NO₃ | 64.87 | 5.22 | 3.15 | 65.28 | 5.04 | 3.21 |
| XXXI | C₂₄H₂₅Cl₂NO₄ | 62.34 | 5.45 | 3.03 | 62.69 | 5.28 | 3.07 |
| XXXII | C₂₄H₂₃Cl₂NO₄ | 62.62 | 5.04 | 3.04 | 63.19 | 4.84 | 3.12 |
| XXXV | C₂₄H₂₂Cl₂O₃ | 67.14 | 5.17 | — | 67.49 | 5.14 | — |
| XXXIII | C₂₄H₂₃Cl₂NO₃ | 64.87 | 5.22 | 3.15 | 65.33 | 5.10 | 3.14 |
| XXXIV | C₂₄H₂₄Cl₂O₃ | 66.83 | 5.61 | — | 66.62 | 5.50 | — |

TABLE III:

Principal Infrared Bands of Pyrethroid Esters (in cm⁻¹)

| Example | Phase | C=O | Others |
|---|---|---|---|
| IV | neat | 1745 | 2955, 1585, 1480, 1445, 1270, 1240, 1205, 1160, 1140, 1110, 860, 695 |
| V | neat | 1750 | 2960, 1610, 1595, 1275, 1240, 1170, 1120 |
| VI | neat | 1745 | 2955, 1610, 1595, 1260, 1170, 1120, 1020, 795 |
| VII | neat | 1730 | 2960, 1620, 1550, 1495, 1455, 1390, 1370, 1160, 1120, 950, 880, 725, 700 |
| VIII | neat | 1730 | 2955, 1550, 1495, 1450, 1395, 1160, 1120, 950, 795, 720, 700 |
| IX | neat | 1745 | 2960, 1635, 1580, 1480, 1440, 1240, 1200, 1160, 1120, 1020, 995, 880, 780, 750, 695 |
| X | neat | 1750 | 2960, 1635, 1585, 1545, 1245, 1205, 1160, 1130, 885, 780, 750, 695 |
| XI | neat | 1750 | 2960, 1630, 1585, 1480, 1445, 1245, 1205, 1120, 1020, 890, 790, 740, 695 |
| XII | neat | 1745 | 2960, 1630, 1585, 1480, 1440, 1240, 1205, 1140, 1110, 1020, 930, 780, 730, 695 |
| XIII | neat | 1745 | 2960, 1580, 1480, 1440, 1240, 1230, 1205, 1140, 1110, 1020, 990, 810, 790, 745, 690 |
| XIV | neat | 1745 | 2955, 1580, 1480, 1440, 1240, 1230, 1205, 1140, 1110, 1020, 990, 810, 790, 750, 690 |
| XV | neat | 1750 | 2960, 1585, 1485, 1445, 1245, 1230, 1205, 1140, 1120, 920, 780, 750, 695 |
| XVI | neat | 1750 | 2960, 1620, 1585, 1485, 1440, 1240, 1205, 1140, 1110, 895, 695 |
| XVII | neat | 1745 | 3070, 3000, 2920, 1618, 1585, 1480, 1440, 1240, 1205, 1160, 1125, 1020, 870, 690 |
| XVIII | neat | 1750 | 3070, 3000, 2960, 2930, 2870, 1620, 1585, 1480, 1450, 1280, 1240, 1210, 1120, 1020, 1000, 900, 860, 690 |
| IX | neat | 1745 | 2960, 2930, 2870, 1620, 1585, 1480, 1440, 1375, 1270, 1240, 1205, 1160, 1140, 1105, 1020, 980, 910, 895, 865, 850, 790, 750, 695 |
| XX | CH₂Cl₂ | 1740 | 2955, 2930, 2860, 1600, 1585, 1480, 1440, 1230, 1205, 1160, 1105, 1020, 1000, 875 |
| XXI | CH₂Cl₂ | 1740 | 2960, 2930, 2870, 1600, 1580, 1480, 1445, 1230, 1210, 1160, 1110, 900, 890 |
| XXII | CH₂Cl₂ | 1740 | 2960, 2930, 2870, 1610, 1580, 1480, 1440, 1230, 1205, 1140, 1110, 910, 890, 860 |
| XXIII | neat | 1745 | 2970, 2940, 2880, 1610, 1585, 1480, |

TABLE III:-continued

| Example | Phase | C=O | Others |
|---|---|---|---|
| | | | 1445, 1260, 1250, 1210, 1160, 1120, 875, 695 |
| XXIV | neat | 1745 | 2960, 2870, 1620, 1590, 1485, 1450, 1380, 1320, 1280, 1260, 1210, 1130, 990, 900, 870, 790, 760, 695 |
| XXV | neat | 1745 | 2970, 1618, 1580, 1485, 1455, 1380, 1320, 1280, 1240, 1220, 1170, 1145, 1110, 1020, 1000, 900, 870, 840, 790, 700 |
| XXVI | neat | 1750 | 3100, 3020, 2990, 2950, 2895, 1620, 1600, 1485, 1455, 1260, 1230, 1205, 1130, 910, 870, 860, 800, 700 |
| XXVII | neat | 1750 | 2970, 1620, 1600, 1495, 1460, 1260, 1220, 1205, 1150, 1120, 1020, 875, 855, 800 |
| XXVIII | $CH_2Cl_2$ | 1755 | 3100, 3000, 2950, 1620, 1595, 1495, 1460, 1240, 1220, 1135, 1100, 1040, 1020, 910, 875, 840, 795 |
| XXIX | neat | 1755 | 2980, 2950, 2900, 1620, 1600, 1510, 1480, 1290, 1260, 1220, 1120, 1025, 1000, 910, 880, 700 |
| XXX | neat | 1760 | 2980, 1610, 1595, 1510, 1495, 1260, 1220, 1180, 1125, 1020, 918, 870, 830, 700 |
| XXXI | neat | 1760 | 2980, 2950, 1620, 1600, 1510, 1495, 1470, 1460, 1290, 1270, 1240, 1215, 1190, 1155, 1120, 1050, 1020, 880, 850 |
| XXXII | neat | 1740 | 2980, 1610, 1590, 1500, 1450, 1250, 1125, 1020, 915, 870, 845, 795 |
| XXXIII | neat | 1740 | 2880, 1610, 1580, 1480, 1435, 1250, 1220, 1130, 1025, 875, 800, 690 |
| XXXV | neat | 1740 | 3080, 3050, 3010, 2980, 1610, 1590, 1490, 1450, 1250, 1220, 1140, 1030, 910, 795 |

TABLE IV

| Example | Structure | Aphid | Mite | SAW | MBB | HF |
|---|---|---|---|---|---|---|
| * | Cl₂C=CH-CH₂CHCO₂CH(CN)(iPr)-C₆H₄-O-C₆H₅ | 5 | 330 | 70 | 24 | 60 |
| IV | Cl₂C=CH-CH(CH₃)-CHCO₂CH(CN)(iPr)-C₆H₄-O-C₆H₅ | 0.5 | 200 | 104 | 3 | 38 |
| XIX | Cl₂C=CH-CH(CH₂CH₃)-CHCO₂CH(CN)(iPr)-C₆H₄-O-C₆H₅ | 4 | 250 | ~500 | 19 | 500 |
| XX | Cl₂C=CH-C(CH₃)₂-CHCO₂CH(CN)(iPr)-C₆H₄-O-C₆H₅ | >500 | 1 | >500 | ~500 | 1 |
| XVII | Cl₂C=CH-CH₂CHCO₂CH(CN)(cyclopropyl)-C₆H₄-O-C₆H₅ | 11 | >500 | >500 | >500 | >500 |
| XVIII | Cl₂C=CH-CH(CH₃)-CHCO₂CH(CN)(cyclopropyl)-C₆H₄-O-C₆H₅ | 0.4 | 250 | 25 | 3 | 39 |
| * | Cl₂C=CH-CH₂CHCO₂CH(CN)(Et)-C₆H₄-O-C₆H₅ | 16 | >500 | >500 | >500 | >500 |
| XXII | Cl₂C=CH-CH(CH₃)-CHCO₂CH(CN)(Et)-C₆H₄-O-C₆H₅ | 4 | ~120 | 49 | 9 | 66 |

TABLE IV-continued

| Example | Structure | Aphid | Mite | SAW | MBB | HF |
|---------|-----------|-------|------|-----|-----|-----|
| XXIII | 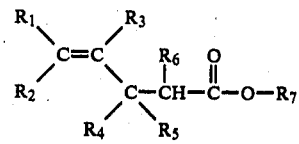 | ~500 | >500 | >500 | >100 | >500 |

*Prior Art Compounds disclosed by Belgium patent 860,887

It will be understood that the insect species and other pests employed in the above tests are merely representative of a wide variety of pests that can be controlled by use of the novel compounds of this invention.

The compounds contemplated in this invention may be applied as insecticides, miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylene oxides with phenol and organic acids, alkyl aryl sulfonates, complex ether alcohols, quaternary ammonium compounds, and the like may be employed for this purpose.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects, mites upon plants or other material to which the pesticides are applied. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are compatible with other constitutents of the spray schedule, and they may be used in the soil, upon the seeds, or the roots of plants without injuring either the seeds or roots of plants. Mixtures of the active compounds may be employed if desired as well as combinations of the activecompounds of this invention with other biologically active compounds.

What is claimed is:

1. A composition of the formula:

$$\begin{array}{c} R_1 \\ \diagdown \\ R_2 \diagup \end{array} C = C \begin{array}{c} R_3 \\ \diagup \\ \diagdown \\ C - CH - C - O - R_7 \\ \diagup \diagdown \\ R_4 \quad R_5 \end{array} \begin{array}{c} R_6 \quad O \\ | \quad \| \end{array}$$

wherein $R_1$, $R_2$, and $R_3$ are independently H, a lower alkyl group having from 1 to 3 carbon atoms or halogen;

$R_4$ and $R_5$ are independently H, a lower alkyl group having from 1 to 3 carbon atoms, polyhaloalkyl, haloalkyl, halogen, a lower alkenyl group having from 2 to 3 carbon atoms, a lower cycloalkyl group having from 3 to 5 carbon atoms, a lower cycloalkenyl group having from 3 to 5 carbon atoms, cyano, nitro, a lower alkoxy group having from 1 to 3 carbon atoms, arloxy, a lower alkylthio group having from 1 to 3 carbon atoms, arylthio, a lower alkylsulfinyl group having from 1 to 3 carbon atoms, arylsulfinyl, a lower alkylsulfinyl group having from 1 to 3 carbon atoms, arylsulfonyl, acylamido, or a lower dialkylamino group having from 1 to 3 carbon atoms;

$R_6$ is selected from the group consisting of: (1) cycloalkyl, alkenyl, branched alkenyl, or cycloalkenyl; or (2) a branched alkyl group having from 3 to 5 carbon atoms or an alkyl group having from 1 to 5 carbon atoms, with the proviso that $R_4$ or $R_5$ is other than hydrogen.

$R_7$ is a member selected from the group consisting of:

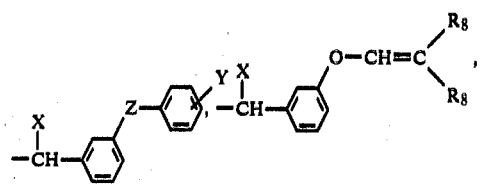

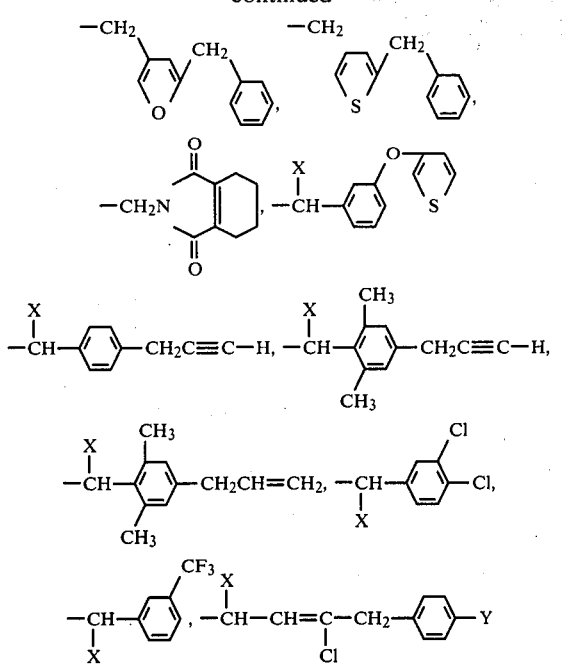

wherein:
X is hydrogen, cyano, ethynyl, thiamido, a lower alkyl group having from 1 to 3 carbon atoms, a lower cycloalkyl group having from 3 to 5 carbon atoms, a lower alkenyl group having from 2 to 5 carbon atoms, a low cycloalkenyl group having from 3 to 5 carbon atoms or polyhaloalkyl;

Y is hydrogen, a lower alkyl group having from 1 to 3 carbon atoms, polyhaloalkyl, haloalkyl, halogen, cyano, nitro, a lower alkoxy group having from 1 to 3 carbon atoms, aryloxy, a lower alkylthio group having from 1 to 3 carbon atoms, arylthio, a lower alkylsulfinyl group having from 1–3 carbon atoms, arylsulfonyl, alkylsulfonyl, acylamido, or a lower dialkylamino group having from 1 to 3 carbon atoms;

$R_8$ is bromine or chlorine; and

Z is oxygen, sulfur or its oxides, or methylene.

2. A composition as defined in claim 1 wherein only one of $R_4$ or $R_5$ is methyl.

3. A composition as defined in claim 1 wherein $R_1$ and $R_2$ are halogen, only one of $R_4$ or $R_5$ is methyl and $R_6$ is isopropyl or cyclopropyl.

4. A composition as defined in claim 3 wherein $R_3$ and one of $R_4$ or $R_5$ are hydrogen and $R_1$ and $R_2$ are chlorine or bromine.

5. (α-cyano-m-phenoxybenzyl) 5,5-dichloro-3-methyl-2-cyclopropyl-4pentenoate.

6. (α-cyano-m-phenoxybenzyl) 5,5-dichloro-3-methyl-2-isopropyl-4-pentenoate.

7. [α-cyano-m-(4-chloro-ophenoxy) benzyl] 5,5-dichloro-3-methyl-2-isopropyl-4-pentenoate.

8. A pesticide composition comprising an acceptable carrier and an insecticidally or miticidally effective amount of a compound of the formula:

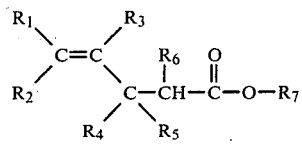

wherein:
$R_1$, $R_2$, and $R_3$ are independently H, a lower alkyl group having from 1 to 3 carbon atoms or halogen;

$R_4$ and $R_5$ are independently H, a lower alkyl group having from 1 to 3 carbon atoms, polyhaloalkyl, haloalkyl, halogen, a lower alkenyl group having from 2 to 3 carbon atoms, a lower cycloalkyl group having from 3 to 5 carbon atoms, a lower cycloalkenyl group having from 3 to 5 carbon atoms, cyano, nitro, a lower alkoxy group having from 1 to 3 carbon atoms, arloxy, a lower alkylthio group having from 1 to 3 carbon atoms, arylthio, a lower alkylsulfinyl group having from 1 to 3 carbon atoms, arylsulfinyl, a lower alkylsulfonyl group having from 1 to 3 carbon atoms, arylsulfonyl, acylamido, or a lower dialkylamino group having from 1 to 3 carbon atoms;

$R_6$ is selected from the group consisting of: (1) cycloalkyl, alkenyl, branched alkenyl, or cycloalkenyl; or (2) a branched alkyl group having from 3 to 5 carbon atoms or an alkyl group having from 1 to 5 carbon atoms, with the proviso that $R_4$ or $R_5$ is other than hydrogen.

$R_7$ is a member selected from the group consisting of:

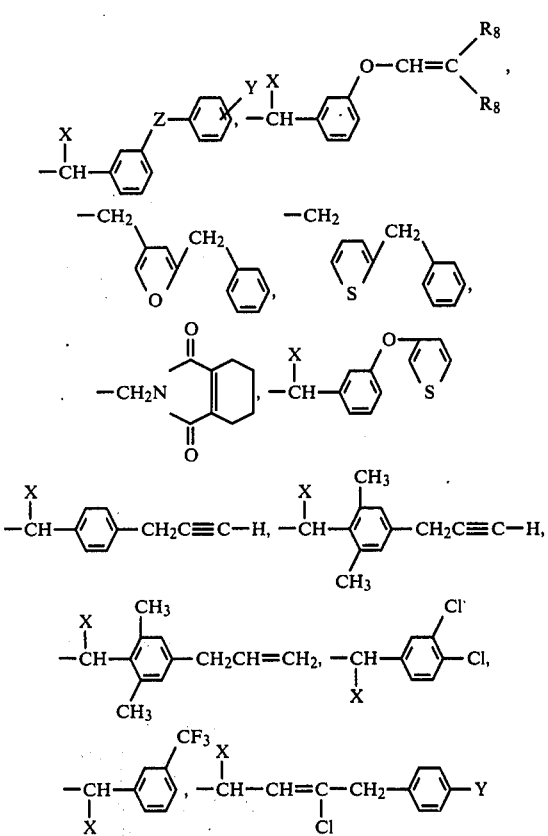

wherein:

X is hydrogen, cyano, ethynyl, thiamido, a lower alkyl group having from 1 to 3 carbon atoms, a lower cycloalkyl group having from 3 to 5 carbon atoms, a lower alkenyl group having from 2 to 5 carbon atoms, a low cycloalkenyl group having from 3 to 5 carbon atoms or polyhaloalkyl;

Y is hydrogen, a lower alkyl group having from 1 to 3 carbon atoms, polyhaloalkyl, haloalkyl, halogen, cyano, nitro, a lower alkoxy group having from 1 to 3 carbon atoms, aryloxy, a lower alkylthio group having from 1 to 3 carbon atoms, arylthio, a lower alkylsulfinyl group having from 1–3 carbon atoms, arylsulfonyl, alkylsulfonyl, acylamido, or a lower dialkylamino group having from 1 to 3 carbon atoms;

$R_8$ is bromine or chlorine; and

Z is oxygen, sulfur or its oxides, or methylene.

9. A pesticide composition as defined in claim 8 wherein only one of $R_4$ or $R_5$ is methyl.

10. A pesticide composition as defined in claim 8 wherein $R_1$ and $R_2$ are halogen, only one of $R_4$ or $R_5$ is methyl and $R_6$ is isopropyl or cyclopropyl.

11. A pesticide composition as defined in claim 10 wherein $R_3$ and one of $R_4$ or $R_5$ are hydrogen and $R_1$ and $R_2$ are chlorine or bromine.

12. A pesticide composition as defined in claim 11 wherein $R_7$ is

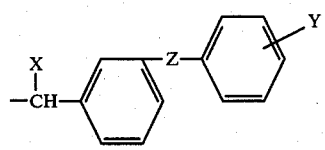

13. A pesticide composition as defined in claim 12 wherein X is cyano, Y is hydrogen and Z is oxygen.

14. A pesticide composition as defined in claim 8 wherein said composition is:
(α-cyano-m-phenoxybenzyl) 5,5-dichloro-3-methyl-2-cyclopropyl-4-pentenoate.

15. A pesticide composition as defined in claim 8 wherein said composition is
(α-cyano-m-phenoxybenzyl) 5,5-dichloro-3-methyl-2-isopropyl-4-pentenoate.

16. A pesticide composition as defined in claim 8 wherein saied composition is:
[α-cyano-m-(4-chloroophenoxy) benzyl] 5,5-dichloro-3-methyl-2-isopropyl-4-pentenoate.

17. A method of controlling insects and mites which comprises subjecting them to a lethal amount of a composition of the formula:

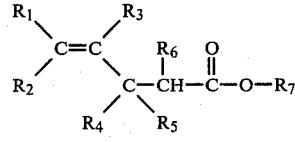

wherein
$R_1$, $R_2$, and $R_3$ are independently H, a lower alkyl group having from 1 to 3 carbon atoms or halogen;
$R_4$ and $R_5$ are independently H, a lower alkyl group having from 1 to 3 carbon atoms, polyhaloalkyl, haloalkyl, halogen, a lower alkenyl group having from 2 to 3 carbon atoms, a lower cycloalkyl group having from 3 to 5 carbon atoms, a lower cy-cloalkenyl group having from 3 to 5 carbon atoms, cyano, nitro, a lower alkoxy group having from 1 to 3 carbon atoms, arloxy, a lower alkylthio group having from 1 to 3 carbon atoms, arylthio, a lower alkylsulfinyl group having from 1 to 3 carbon atoms, arylsulfinyl, a lower alkylsulfonyl group having from 1 to 3 carbon atoms, arylsulfonyl, acylamido, or a lower dialkylamino group having from 1 to 3 carbon atoms;

$R_6$ is selected from the group consisting of: (1) cycloalkyl, alkenyl, branched alkenyl, or cycloalkenyl; or (2) a branched alkyl group having from 3 to 5 carbon atoms or an alkyl group having from 1 to 5 carbon atoms, with the proviso that $R_4$ or $R_5$ is other than hydrogen;

$R_7$ is a member selected from the group consisting of:

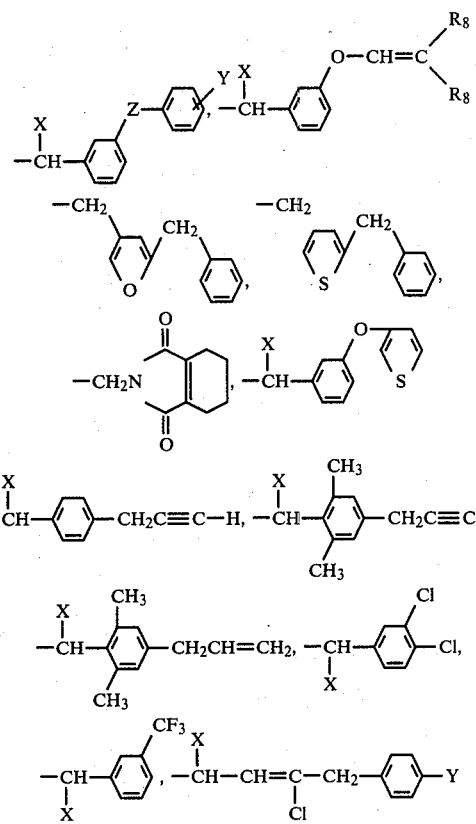

wherein:
X is hydrogen, cyano, ethynyl, thiamido, a lower alkyl group having from 1 to 3 carbon atoms, a lower cycloalkyl group having from 3 to 5 carbon atoms, a lower alkenyl group having from 2 to 5 carbon atoms, a low cycloalkenyl group having from 3 to 5 carbon atoms or polyhaloalkyl;

Y is hydrogen, a lower alkyl group having from 1 to 3 carbon atoms, polyhaloalkyl, haloalkyl, halogen, cyano, nitro, a lower alkoxy group having from 1 to 3 carbon atoms, aryloxy, a lower alkylthio group having from 1 to 3 carbon atoms, arylthio, a lower alkylsulfinyl group having from 1–3 carbon atoms, arylsulfonyl, alkylsulfonyl, acylamido, or a lower dialkylamio group having from 1 to 3 carbon atoms;

$R_8$ is bromine or chlorine; and

Z is oxygen, sulfur or its oxides, or methylene.

18. A method as defined in claim 17 wherein only one of $R_4$ or $R_5$ is methyl.

19. A method as defined in claim 17 wherein $R_1$ and $R_2$ are halogen, only one of $R_4$ or $R_5$ is methyl and $R_6$ is isopropyl or cyclopropyl.

20. A method as defined in claim 19 wherein $R_3$ and one of $R_4$ or $R_5$ are hydrogen and $R_1$ and $R_2$ are chlorine or bromine.

21. A method as defined in claim 17 wherein said composition is:

(α-cyano-m-phenoxybenzyl) 5,5-dichloro-3-methyl-2-isopropyl-4-pentenoate.

22. A method as defined in claim 17 wheren said composition is:

[α-cyano-m-(4-chlorophenoxy) benzyl] 5,5-dichloro-3-methyl-2-isopropyl-4-pentenoate.

23. A method of controlling insects and mites which comprises subjecting them to a lethal amount of (α-cyano-m-phenoxybenzyl) 5,5-dichloro-3-methyl-2-cyclopropyl-4-pentenoate.

* * * * *

UNITED STATES PATENT AND TRADEMARK OFFICE
CERTIFICATE OF CORRECTION

PATENT NO. : 4,291,057
DATED : September 22, 1981
INVENTOR(S) : T.N. Wheeler

It is certified that error appears in the above—identified patent and that said Letters Patent is hereby corrected as shown below:

Column 25: after TABLE IV; delete "Belgium patent 860,887". insert -- Belgium Patent 860,687 --

Column 26: line 49: before "group", delete "alkylsulfinyl" insert -- alkylsulfonyl --

Column 27: line 5 delete

"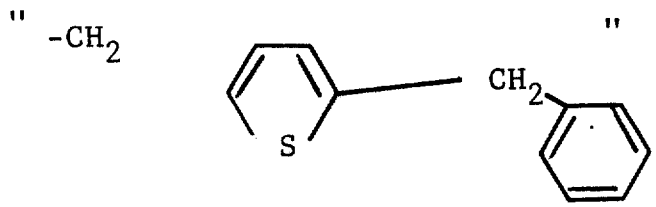"

insert:

-- 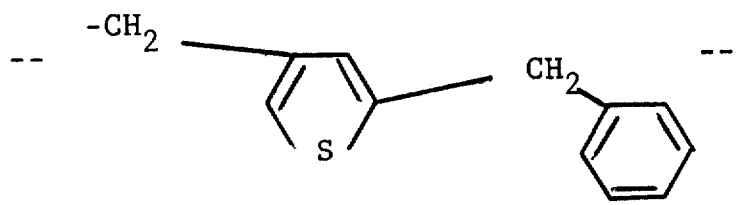 --

Signed and Sealed this

Tenth Day of May 1983

[SEAL]

Attest:

GERALD J. MOSSINGHOFF

Attesting Officer        Commissioner of Patents and Trademarks